United States Patent
Rizzi

(10) Patent No.: US 10,507,451 B2
(45) Date of Patent: Dec. 17, 2019

(54) SONICATION IN A UREA OR MELAMINE SYNTHESIS PROCESS

(71) Applicant: Casale SA, Lugano (CH)

(72) Inventor: Enrico Rizzi, Casnate con Bernate (IT)

(73) Assignee: Casale SA (CH)

( * ) Notice: Subject to any disclaimer, the term of this patent is extended or adjusted under 35 U.S.C. 154(b) by 0 days.

(21) Appl. No.: 15/563,460

(22) PCT Filed: Mar. 11, 2016

(86) PCT No.: PCT/EP2016/055264
§ 371 (c)(1),
(2) Date: Sep. 29, 2017

(87) PCT Pub. No.: WO2016/156015
PCT Pub. Date: Oct. 6, 2016

(65) Prior Publication Data
US 2018/0071708 A1    Mar. 15, 2018

(30) Foreign Application Priority Data

Mar. 30, 2015 (EP) .................................. 15161665

(51) Int. Cl.
*B01J 19/10* (2006.01)
*B01J 19/24* (2006.01)
*C07C 273/04* (2006.01)
*C07C 273/12* (2006.01)

(52) U.S. Cl.
CPC .............. *B01J 19/10* (2013.01); *B01J 19/246* (2013.01); *C07C 273/04* (2013.01); *C07C 273/12* (2013.01); *B01J 2219/0877* (2013.01); *Y02P 20/142* (2015.11); *Y02P 20/582* (2015.11)

(58) Field of Classification Search
CPC .. B01J 19/10; B01J 19/246; B01J 2219/0877; C07C 273/04; C07C 273/12; Y02P 20/142; Y02P 20/582
USPC ....................................... 204/157.62, 157.81
See application file for complete search history.

(56) References Cited

U.S. PATENT DOCUMENTS

| | | | | |
|---|---|---|---|---|
| 3,325,386 A | * | 6/1967 | Jurschewitz | B01J 19/10 204/193 |
| 5,164,094 A | * | 11/1992 | Stuckart | B01J 19/10 204/157.15 |
| 5,304,353 A | * | 4/1994 | Dente | B01D 3/20 202/158 |
| 6,815,545 B2 | | 11/2004 | Bucka et al. | |
| 7,041,822 B2 | | 5/2006 | Coufal | |

(Continued)

FOREIGN PATENT DOCUMENTS

| | | | |
|---|---|---|---|
| CN | 103601693 A | * | 2/2014 |
| KR | 2009 0029375 A | | 3/2009 |

(Continued)

OTHER PUBLICATIONS

Machine translation of description of CN103601693A (Year: 2014).*

(Continued)

*Primary Examiner* — Nicholas A Smith
*Assistant Examiner* — Colleen M Raphael
(74) *Attorney, Agent, or Firm* — Akerman LLP

(57) ABSTRACT

Process and respective reactor for urea or melamine synthesis, comprising sonication treatment of at least part of a reaction liquid mass or two-phase mixture contained inside said reactor.

6 Claims, 2 Drawing Sheets

(56) References Cited

U.S. PATENT DOCUMENTS

| | | | |
|---|---|---|---|
| 7,094,927 B2* | 8/2006 | Tjioe | C07C 273/12 |
| | | | 422/129 |
| 2004/0022695 A1* | 2/2004 | Simon | B01J 19/10 |
| | | | 422/128 |
| 2004/0256213 A1* | 12/2004 | Marhasin | B01J 19/10 |
| | | | 204/157.42 |
| 2009/0166177 A1* | 7/2009 | Wenzel | B01J 19/24 |
| | | | 204/157.62 |
| 2011/0091369 A1* | 4/2011 | Casara | B01D 53/58 |
| | | | 423/356 |

FOREIGN PATENT DOCUMENTS

| | | | |
|---|---|---|---|
| WO | 2005/102992 A1 | 11/2005 | |
| WO | 01/30748 A1 | 5/2011 | |
| WO | 2011/161215 A1 | 12/2011 | |

OTHER PUBLICATIONS

Machine translation of claims of CN103601693A (Year: 2014).*
International Search Report dated May 27, 2016 in connection with PCT/EP2016/055264.
International Preliminary Report on Patentability dated Jun. 29, 2017 in connection with PCT/EP2016/055264.

* cited by examiner

SONICATION IN A UREA OR MELAMINE SYNTHESIS PROCESS

This application is a national phase of PCT/EP2016/055264, filed Mar. 11, 2016, and claims priority to EP 15161665.3, filed Mar. 30, 2015, the entire contents of both of which are hereby incorporated by reference.

FIELD OF APPLICATION

The invention relates to the field of chemical reactors and processes for urea or melamine synthesis.

PRIOR ART

Processes and relative plants for urea synthesis from ammonia ($NH_3$) and carbon dioxide ($CO_2$) and processes for melamine synthesis from urea, to which the present invention relates, are described in the literature. For example, a description of processes and plants for urea synthesis is provided in Ullmann's Encyclopedia of Industrial Chemistry, Wiley-VCH Verlag, vol. A27; a description of melamine processes and plants is provided in Ullmann's Encyclopedia of Industrial Chemistry, 6th ed., vol. 21, p. 205. Melamine plants are often combined with urea plants since the synthesis of melamine provides a stream of gases (offgases) containing ammonia and carbon dioxide which can be reused as reagents to produce urea.

The preparation of urea is also described in WO 01/30748 and WO 2005/102992.

The aforementioned urea and melamine synthesis processes are nowadays still object of study and efforts are being made to improve them The synthesis of urea takes place in a urea reactor which is essentially a heterogeneous vapour/liquid system. The vapour phase contains mainly free $CO_2$ and ammonia; the liquid phase contains $NH_3$, carbamate, bicarbonate, urea and water. The reagents are transferred gradually from the vapour phase to the liquid phase, where the $CO_2$ reacts with $NH_3$, producing carbamate and then urea and water, with a continuous exchange of $CO_2$ and $NH_3$ between the two phases.

It is known that the formation of urea involves the following phenomena: mass transfer between the bubbles containing vapour and the liquid, at the vapour/liquid interface, with carbamate production and heat generation; mass and heat transfer from the vapour/liquid interface to the vapour/liquid emulsion and from the latter to the liquid, with carbamate conversion into urea.

Therefore, urea reactors aim to obtain good mass and heat transfer especially at the vapour/liquid interface. In the prior art, in order to satisfy this requirement, a certain residence time in the reactor is calculated so as to maximize the quantity of vapour transferred to the liquid phase, trying to minimize the vapours containing $NH_3$ and $CO_2$ at the reactor outlet. However, it has been found that these undesirable vapours are always present in the flow leaving the reactor owing to the limitations in the mass and heat transfer which slow down the reaction.

Another problem which is encountered during urea synthesis arises from the fact that $CO_2$ is less soluble in water than ammonia and urea. In order to overcome this drawback, in the prior art a $NH_3$ over $CO_2$ ratio is used, which is substantially greater than the stoichiometric ratio of 2:1, for example a ratio of 3:1 or greater. Moreover it is known that the conversion yield per single passage is low, this resulting in the transition from the initial once-through processes to the current stripping processes, which comprise medium and low pressure recovery sections, but are however considerably complex and costly.

A stripping plant typically comprises a synthesis section including a reactor, a stripper, a condenser and a scrubber. Said apparatuses operate at high pressure and temperature and with corrosive fluids and therefore require high-cost materials and construction solutions. In other words, owing to the low conversion yield inside the reactor, it is required to introduce other apparatuses downstream of the reactor (e.g. stripper and condenser) which are very costly.

The synthesis of melamine has similar problems of mass and heat transfer in the liquid phase and mixing at the vapour/liquid interface. The melamine plants comprise a first synthesis reactor (also called primary reactor or melamine reactor) and a second stripping reactor. The primary reactor performs the endothermic conversion of the liquid urea into melamine; the effluent of said primary reactor is directed to the secondary reactor, where it undergoes a process of stripping using gaseous ammonia.

The primary reactor is a reactor with internal recirculation and generally comprises a heating bundle arranged in the form of an annular ring around a shell; an external stream of urea feed and a recirculating stream from the zone of the heating bundle converge inside the shell.

The typical configurations of the prior art for a primary melamine reactor and a secondary melamine reactor are described in U.S. Pat. Nos. 6,815,545 and 7,041,822, respectively. A combined reactor, which combines the functions of primary reactor, secondary reactor and scrubber in a single pressurised body, is described in WO 2011/161215.

KR 2009 0029375 discloses a sonication system for preparation of 5-ortho-tolylpentene from ortho-xylene and alkali metal catalyst.

SUMMARY OF THE INVENTION

The invention aims to improve the processes and apparatuses for urea and melamine synthesis. In particular, the invention aims to overcome the aforementioned problems and technological obstacles.

The idea forming the basis of the invention is to use the technique of sonication in the processes and apparatuses for urea and melamine synthesis. The term "sonication" denotes that at least part of a liquid or of a two-phase mixture (liquid and gas) contained in a reactor is subjected to sound waves.

The objects of the invention are therefore achieved with a process according to claim 1. Another aspect of the invention relates to a reactor designed to apply sonication to the synthesis reaction of urea or melamine. Preferably said reactor is a non-catalytic reactor.

Preferably the invention uses sonication with waves having a frequency comprised between 1 kHz and 1 MHz, although waves having even higher frequency may be used.

Preferably, the sonication is performed at ultrasound frequency, i.e. at least 20 kHz or more; preferably in the range of 20 kHz to 1 MHz, more preferably 20 kHz to 100 kHz and even more preferably 20 kHz to 40 kHz.

The sonication is preferably generated using one or more waves sources, the sources being electrical or mechanical.

An electrical source for example comprises an active element, such as a probe or a membrane, which vibrates at a predetermined frequency, and transmits vibrations to the surrounding liquid which are propagated within the liquid in the form of sound waves. A mechanical source operates according to the principle of cavitation and generally uses a dedicated rotor able to induce cavitation phenomena in the fluid. The mechanical sources are designed to treat larger volumes of fluid.

Since the transmission of sound waves is subjected to attenuation phenomena, preferably the sonication is performed inside a small volume, for example inside a sonication chamber. Advantageously, said sonication chamber has a significantly smaller volume than the volume of the reactor. One advantage of performing said treatment inside a chamber with small dimensions is the reduction of the power of the sound waves generator, for the same treatment efficiency, and consequently a reduction in the cost.

In a reactor with a sonication chamber, the sound waves source is contained inside said sonication chamber or, alternatively, said source is in directed communication with said sonication chamber. In order to treat all the fluid, it is convenient to circulate or recirculate all the fluid through said sonication chamber.

In a preferred embodiment, for example, said sonication chamber is delimited by a vertical-axis cylindrical wall which is coaxial with the shell of the reactor. More advantageously, the chamber is open at the bottom and open at the top, so as to allow a continuous recirculating movement of the liquid phase (or two phases) between the inside of the chamber and the surrounding zone. The fluid enters through one of two open ends (e.g. bottom end) and exits from the opposite end (e.g. top end). Passing through the chamber, the fluid is subjected to the action of the sound waves and undergoes the desired sonication treatment. Owing to the recirculation, all the fluid mass is gradually acted on by the sound waves, despite the small size of the sound waves generator and the respective sonication chamber.

The treatment inside a sonication chamber is facilitated in the recirculation reactors. Owing to recirculation, it is in fact easier to subject all the fluid to the sonication treatment, even though the sound waves are located in a relatively small zone of the reactor. The invention is applicable to both urea and melamine recirculation reactors. In particular, a preferred application relates to melamine recirculation reactors already comprising an inner shell which defines a reaction zone and a recirculation zone which are coaxial and concentric. These reactors may be revamped in order to implement the invention, for example by providing one or more sonication sound waves generators in the zone bounded by the inner shell.

In once-through reactors, which are typically smaller than recirculation reactors, the sonication may be applied to the entire reactor volume, namely in these cases the sonication volume is equivalent to the total volume of the reactor. In a once-through reactor, a preferred seat for a source device of the sonication waves is situated at or close to the inlet opening.

By applying sonication in an open volume, the treatment is more efficient inside a given area of influence of the sonicator or sonicators. Another aspect of the invention consists in providing at least one mechanical stirrer able to cause the movement of the fluid and transfer it into the area of influence of the sonicator or sonicators. In this way the phenomenon of attenuation of the sound waves is counteracted and the sonication treatment is rendered more uniform. Mechanical stirring constitutes a preferred characteristic, but it is not indispensable. In some embodiments, for example inside the melamine reactor, the desired circulation occurs owing to the differences in density, which are also due to the formation of gas bubbles following the reaction which takes place inside the sonication chamber.

The applicant has found that the application of sonication is particularly advantageous for the synthesis reactions of urea and melamine, in which the conversion efficiency is improved.

The advantages of the invention comprise essentially:

greater interface between liquid/vapour phases, in two-phase systems;

greater conversion efficiency;

acceleration of chemical reactions, reduction in reaction times;

reduction in reaction by-products.

Without being bound by theory, it is considered that this beneficial effect is due to cavitation phenomena caused by the sound waves (sonic cavitation). The tem "cavitation" denotes the formation of gas bubbles which implode in the liquid phase and locally generate (in a very small volume) very high pressures and temperatures. For example, and without this being understood as limiting, the sonic cavitation may locally induce a temperature of around 5000 K and a pressure of around 500 bar.

The sonication and consequent cavitation have the effect of improving the mass and heat transfer from the vapour phase to the liquid phase and consequently increasing the carbamate to urea conversion. In urea reactors, the applicant has found that the application of sonication increases the solubility of the $CO_2$ and allows achieve a good conversion with a $NH_3:CO_2$ ratio lower than the prior art, i.e. closer to the stoichiometric value of 2.

Owing to these advantages, the technology of the reactors and the respective synthesis sections may be simplified, for example as regards the interiors and/or the materials and/or the dimensions, with cost savings. For example, the fact of improving the conversion in the reactor may result in a reduction of the costs of the apparatuses downstream of the reactor itself.

The advantages will emerge even more clearly with the aid of the detailed description below relating to a number of preferred embodiments.

DETAILED DESCRIPTION

Figure 1:
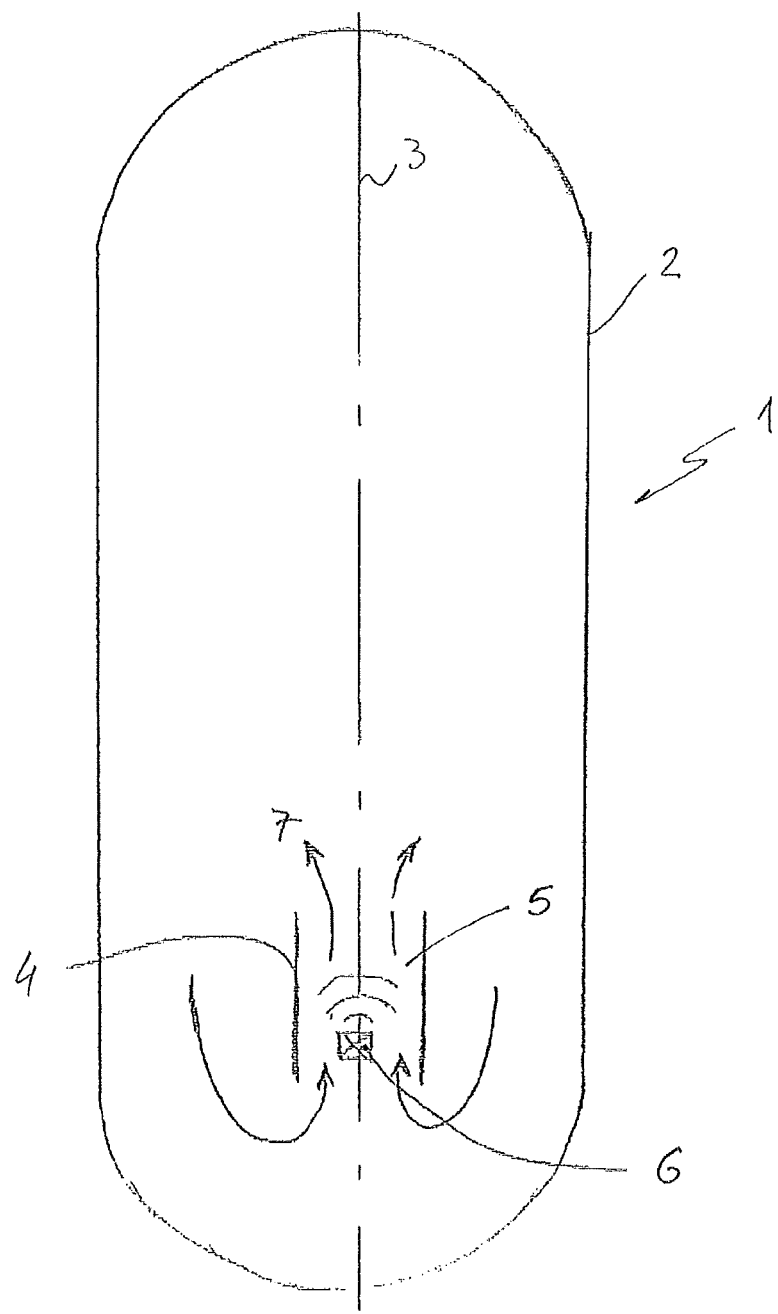
FIG. 1 is a schematic illustration of a recirculating reactor for urea or melamine synthesis, designed to implement the invention.

FIG. 1 shows a general diagram of the reactor 1 according to the invention. The reactor 1 comprises a shell 2 with a vertical axis 3 and an inner shell 4 which is open at the top and bottom. Said shell 4 preferably is cylindrical with a vertical axis, like the outer shell 2. More advantageously, said shell 4 is coaxial with the shell 2, i.e. has the same vertical axis 3.

Said inner shell 4 defines a chamber 5 inside which at least one sonication waves source 6 is installed.

The reactor 1 contains a liquid phase which recirculates through the chamber 5 and in this way is subjected to the action of the sound waves emitted by said source 6. The arrows 7 in FIG. 1 indicate the recirculation of the liquid; owing to said recirculation, the substantially entire liquid mass contained inside the reactor 1 is subjected to the sonication process, notwithstanding the volume of the chamber 5 is significantly smaller than the internal volume of the reactor 1.

Figure 2:
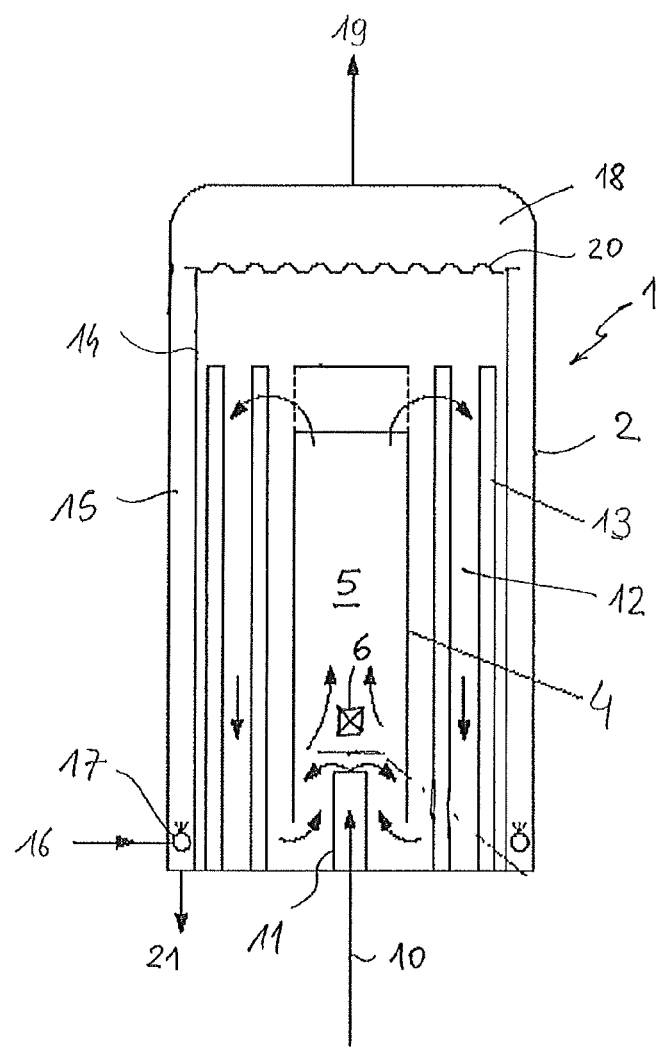
FIG. 2 shows a more detailed diagram of a mode of implementing the invention and relates to a melamine reactor.

FIG. 2 shows in greater detail an embodiment of the invention applied to melamine reactors. For the sake of simplicity, the details which are similar to those of FIG. 1 are indicated with the same reference numbers. In the reactor according to FIG. 2, the wall (or tube) 4 defines a central chamber 5 which forms the primary reaction zone fed with the urea melt 10 via a duct 11. The annular chamber 12, situated around the central chamber 5, forms a recirculation zone for the liquid. Heating elements 13, for example tubes, are housed inside said recirculation chamber 12.

The reactor in FIG. 2 comprises a further shell 14 delimiting an outer wall of the recirculation chamber 12 and also defining a secondary reaction chamber 15, between the shells 2 and 14, fed with gaseous ammonia 16 via a toroidal distributor 17 located on the bottom of said chamber.

The top part of the reactor comprises a top-end chamber 18 which collects the gases released inside the chambers 5, 12 and 15, mainly comprising $NH_3$ and $CO_2$. Said gases form a stream 19 of offgases which is carried away towards a scrubber.

The sound waves source 6 is situated preferably inside the central chamber 5. In this way the sonication affects the liquid phase which recirculates inside the chamber 5, mixing with the urea melt 10.

The reactor according to FIG. 2 operates in the following manner. The liquid melamine circulates with an ascending movement inside the reaction zone 5 and with a descending movement inside the recirculating zone 12, which is also heated by the action of the bodies 13. A recirculation in the direction of the arrows shown in the figures is thus created. It should be noted that, owing to the recirculating movement, the sonication affects all the liquid mass recirculating in the reactor, despite the fact that the source 6 is located only in a specific zone, i.e. inside the primary zone 5 which is directly fed with the urea melt 10.

During normal operation the liquid melamine reaches the level indicated in the figure by the line 20 and flows over the top edge of the shell 14, passing into the peripheral chamber 15. Inside said chamber 15, the liquid melamine undergoes stripping owing to the counter-flow of gaseous ammonia 16 fed from the toroidal distributor 17. The stripped melamine 21 is collected at the bottom of said chamber 15; the gases released during the process—which contain $CO_2$ and ammonia—are collected in the top chamber 18 and discharged from the line 19 towards a scrubber.

The invention may be subjected to variations. For example, with reference to FIG. 2, the sound waves source may be located inside the recirculation chamber 12. The sound waves source 6 may be of the electronical or mechanical type. Said source may be formed, in an equivalent manner, with a plurality of sources.

The example in FIG. 2 shows a melamine reactor which comprises internally the primary reaction zone, inside the central chamber 5 and the recirculation chamber 12, and the secondary or stripping reaction zone, inside the annular chamber 15. The invention, however, is also applicable to conventional reactors which comprise only the primary reaction zone. In this case, stripping with ammonia is performed in an external reactor. In other embodiments, which also fall within the scope of the present invention, the scrubber of the offgases 19 may be incorporated in the same reactor, for example incorporated in the top part of the reactor 1.

The invention claimed is:

1. A process for the synthesis of melamine from urea, inside a chemical reactor, said process comprising a sonication treatment of at least part of a reaction liquid mass or two-phase mixture contained inside said chemical reactor,
   wherein the sonication treatment is performed in a sonication zone inside said chemical reactor,
   wherein the process further comprises the circulation of a liquid phase or liquid/vapour phase through at least one reaction zone and a recirculation zone, which are arranged coaxial and concentric inside said reactor,
   wherein the sonication treatment is performed in at least one of said two reaction and recirculation zones, and
   wherein the reaction zone is a primary reaction zone fed with urea melt.

2. The process according to claim 1, wherein said sound waves have a frequency in the range 1 kHz to 1 MHz.

3. The process according to claim 2, wherein said sound waves have a frequency equal to or greater than 20 kHz.

4. The process according to claim 1, said sound waves being generated by one or more electrical or mechanical sources.

5. The process according to claim 3, wherein said sound waves have a frequency of 20 to 40 kHz.

6. A method, comprising:
   using a sonication treatment inside a reactor for melamine synthesis, wherein said sonication treatment provides transmission of sound waves to at least part of a liquid mass or two-phase mixture contained inside said reactor,
   wherein the sonication treatment is performed in a sonication zone inside said reactor,
   wherein the method further comprises circulating a liquid phase or liquid/vapour phase through at least one reaction zone and a recirculation zone, which are arranged coaxial and concentric inside said reactor,
   wherein the sonication treatment is performed in at least one of said two reaction and recirculation zones, and
   wherein the reaction zone is a primary reaction zone fed with urea melt.

* * * * *